United States Patent [19]
Ofstead

[11] Patent Number: 4,977,901
[45] Date of Patent: Dec. 18, 1990

[54] ARTICLE HAVING NON-CROSSLINKED CRYSTALLIZED POLYMER COATINGS

[75] Inventor: Ronald F. Ofstead, Maplewood, Minn.

[73] Assignee: Minnesota Mining and Manufacturing Company, St. Paul, Minn.

[21] Appl. No.: 505,411

[22] Filed: Apr. 6, 1990

Related U.S. Application Data

[63] Continuation of Ser. No. 275,767, Nov. 23, 1988, abandoned.

[51] Int. Cl.$^5$ ............................................. A61B 5/00
[52] U.S. Cl. .................................... 128/772; 128/657; 428/379; 428/457; 428/463; 606/76
[58] Field of Search ..................... 428/379, 457, 463; 128/657, 772; 606/76

[56] References Cited
U.S. PATENT DOCUMENTS 4,693,939  9/1987  Ofstead .
4,785,059  11/1988  Fydelor et al. .

*Primary Examiner*—Joseph L. Schofer
*Assistant Examiner*—John J. Guarriello
*Attorney, Agent, or Firm*—Donald M. Sell; Walter N. Kirn; Dale A. Bjorkman

[57] ABSTRACT

A non-crosslinked crystallized polymer or polymer blending coating is disclosed for articles that come into contact with bodily fluids. The polymer or polymer blend to be used is crystallizable and is stable in the presence of water at temperatures of up to about 60° C. when in the crystalline state. The polymer or polymer blend is dissolved in a solvent, such as water or dimethyl sulfoxide (DMSO), and is coated on the article. The polymer coating is then crystallized, generally by heat treatment, providing both toughness and increased adherence of the coating to the article without ready dissolution when the article comes into contact with fluids.

13 Claims, No Drawings

ARTICLE HAVING NON-CROSSLINKED CRYSTALLIZED POLYMER COATINGS

This is a continuation of application Ser. No. 07/275,767 filed Nov. 23, 1988 now abandoned

Field of the Invention

This invention relates to a coating for articles that come into contact with bodily fluids.

Background of the Invention

Articles such as diagnostic probes, catheters, guidewires, pacemakers and artificial heart devices have long been inserted in the body for various medical purposes. These articles contact bodily fluids in the normal course of their use, and concerns for toxicity of their composite materials and the potential promotion of thromboembolism formation indicate in many cases that a protective coating is desirable. Also, in the case of certain medical devices and especially of guidewires, it is desirable that the articles should be exceptionally slippery when wet.

Many coating materials have been used in the medical arts. Teflon TM has frequently been used with guidewires in the belief that in addition to increasing the slipperiness of the guidewire, the thrombogenicity of the wire was reduced by the Teflon TM coating. At least one study, however, as reported by Ovitt et al., in Radiology, Vol. 3, p. 43-46, April, 1974, has indicated that fibrin deposits occurred more readily on Teflon TM coated guidewires than on bare stainless steel guidewires U.S. Pat. No. 4,642,267 discloses a coating material which is a polymeric blend of an organic solvent-soluble preformed thermoplastic polyurethane having no reactive isocyanate groups and a second polymer component which is a hydrophilic poly(N-vinyl lactam). The patent hypothesizes that this polymeric blend does not dissipate in water possibly as a result of associative forces with the polyurethane component, chain entanglement or both. The polyurethanes are prepared from isocyanate-capped prepolymers, which may be difficult to completely remove from the ultimate polymeric coating. Additionally, the polymers must be combined by dissolving in solvents disclosed at column 4, lines 53-59 which are undesirable in a medical environment. Experimental preparation of the coatings of this patent have shown that they must be formulated in a substantially anhydrous environment to avoid precipitation of the polyurethane as a particulate solid which yields a grainy coating.

Cross-linked polyvinyl alcohol hydrogels have also been used as coating materials, particularly when bound with heparin as described by Goosen and Sefton in the Journal of Biomedical Materials Research, Vol. 17, p. 359-373, 1983. These polymers are formed using potentially toxic crosslinking agents that are generally undesirable in the medical environment Additionally, the coating materials have a limited useful shelf life because the polymer will form an irreversable gel typically within minutes or hours of addition of the cross-linking agents to the poly(vinyl alcohol). Cross-linked poly(vinyl alcohol) hydrogels have also been used as micromolecular sieves as disclosed in U.S. Pat. No. 3,658,745.

U.S. Pat. No. 4,693,939 discloses a coating made from a non-crosslinked polyvinyl alcohol copolymer wherein the comonomer is selected from vinyl esters, vinyl ethers and copolymerizable di-substituted ethylenes with the resulting copolymer possessing a highly syndiotactic stereochemical configuration This coating is disclosed to be useful for ophthalmic devices due to its great strength. These polymers are difficult to apply as a coating to disparate materials because they do not dissolve readily in a solution below about 130° C. to facilitate coating. Solvent casting, as described at column 8, lines 41-53, yields unacceptable results when coating on metallic objects, because after coating an article with poly(vinyl trifluoroacetate), the coating tends to detach during conversion to poly(vinyl alcohol) by hydrolysis.

SUMMARY OF THE INVENTION

This invention provides a non-crosslinked crystallized polymer or polymer blend coating for articles that come into contact with bodily fluids.

In the practice of this invention, a hydrophilic polymer that is crystallizable and that is stable in the presence of water at temperatures of up to about 60° C. when in the crystalline state is dissolved in a solvent, such as water or dimethyl sulfoxide (DMSO), and coated on the article. The coating is stable if it retains greater than about 50 percent of its tensile strength as measured by conventional testing methods and remains substantially insoluble. The preferred hydrophilic polymers are poly(vinyl alcohol) polymers that are more than about 88% hydrolyzed. The polymer coating is then crystallized by heat treatment, providing both toughness and increased adherence of the coating to the article without ready dissolution when the article comes in contact with fluids. Thus, curing or crosslinking processes are not necessary, because the crystallization serves to insolublize the polymer.

The crystalline physical structure created during the annealing process is sometimes referred to as having "physical cross-links". The polymer coating of this invention is described as being non-crosslinked, which refers only to the absence of chemical cross-links in the polymeric coating.

The polymeric coatings of the present invention are particularly advantageous because the use of toxic cross-linking agents is avoided along with the addition of costly washing steps in the manufacturing process. Also, because no cross-linking agents are introduced to the coating solution, the shelf life of the solution is virtually limitless

DETAILED DESCRIPTION

More specifically, this invention relates to a non-crosslinked, crystallized polymer coating for articles that come into contact with bodily fluids, such as blood, urine, gastrointestinal fluids and cerebrospinal fluid.

The polymeric materials that are used in this invention are hydrophilic polymers that are soluble before crystallization in a solvent at temperatures of less than about 100° C., are capable of being crystallized and that are stable in the presence of water at temperatures of up to about 60° C. when in the crystalline state. A polymer is herein defined to be in a crystalline state if upon analysis a detectable pattern may be observed when using conventional x-ray scattering techniques. Such conventional techniques are disclosed, for example, in "The Structure of Crystalline Polymers", Tadokoro, H. (Wiley Interscience, 1979). Thus, a polymer is "crystallizable" if it is capable of achieving this state. The degree of crystallinity of a polymer is the measurement by weight of the amount of polymer that is in the form of crystallites, as measured by differential scanning calorimetry. Preferably, a polymer has a degree of crystallinity of between about 20 and about 60 percent.

Preferred polymeric materials are poly(vinyl alcohol) materials available as 88% or more hydrolyzed products, where the number refers to the percent of acetate groups removed from the starting polyvinyl acetate polymers. These poly(vinyl alcohol) materials are available from various chemical sources, such as Aldrich Chemical Company (Milwaukee, Wis.). Materials that are less than about 88% hydrolyzed will not readily crystallize, resulting in coatings which actually dissolve in water even if heat treated. The poly(vinyl alcohol) polymer generally has a molecular weight of between about 14,000 and about 1,000,000. Preferably, the poly(vinyl alcohol) polymer has a molecular weight of between about 40,000 and about 126,000, and most preferably the polymer has a molecular weight of between about 80,000 and about 115,000. The preferred crystallized poly (vinyl alcohol) article has a degree of crystallinity of between about 30 and about 50 percent, and more preferably between about 40 and about 45 percent.

Vinyl alcohol copolymers may be used in the practice of this invention. For example, the polyvinyl alcohol polymers with a degree of hydrolysis between 88% and 100% are in fact copolymers of vinyl alcohol and vinyl acetate monomer units. These copolymers function well in the practice of this invention as long as the copolymers are crystallizable as described previously. Other copolymers of vinyl alcohol, for example vinyl alcohol/vinyl butyral, vinyl alcohol/ethylene, vinyl alcohol/acrylic or methacrylic esters may be used as long as the copolymer is able to be crystallized as described previously. The use of dyes or tints, such as those disclosed in U.S. Pat. No. 4,559,059, which are covalently linked to the polyvinyl alcohol polymer material is a further example of the use of copolymers, since the sites of covalent attachment of the dye or tint to the polymer chain represent a structural unit different from the vinyl alcohol units and therefore provide a copolymer structure. It is, of course, possible to prepare such copolymers by the copolymerization of the appropriate vinyl derivative of the dye or tint.

The blending of other polymeric materials with the crystallizable polymer (for example with polyvinyl alcohol) may be done where this creates a desired effect and as long as the presence of the blended polymer component does not interfere with the process of crystallization practiced in this invention. Thus, the addition of the polymer heparin, a polymer normally isolated from mammalian tissue and having molecular weights in the range of from about 3,000 to about 50,000, can be carried out in cases where it may be desired to enhance the antithrombogenic activity of the coating. Such a polymer may be added or blended with the crystallizable polymer to the extent that the presence of the added polymer does not interfere with the crystallization of the crystallizable polymer. A further example of a polymer to blend with the crystallizable polymer is the enzyme trypsin, which can confer enhanced blood compatibility by its proteolytic action upon adsorbed proteinaceous materials which can be involved in thrombus formation. Without being bound by theory, it is thought that such blended polymer components are held within the crystallized polymer by virtue of being entrapped or entangled and do not show evidence of leaching from the crystallized polymer coatings. This behavior is very surprising in that the incorporation of agents such as heparin (or enzymes) is customarily accomplished by difficult and costly chemical modification of either the heparin (or enzymes) or modification of the material to which these agents are to be bound. Modification of such agents as heparin or enzymes can diminish the activity of such material by the change in chemical structures required by the modification processes. The direct incorporation of such agents by blending in the process of this invention avoids these disadvantages while leading to compositions from which the polymeric agent does not leach.

In preparing a polymer coating, the polymeric material is first dissolved in a non-toxic solvent such as water or dimethyl sulfoxide (DMSO) in an amount of about 1 to about 25 percent polymer solids in solvent by weight. Preferably, the polymer/solvent mixture is formulated in the range of about 5 to about 15 percent polymer solids by weight in solvent. The selection of percentage of polymer solids in the coating solution is largely determined by the molecular weight of the selected polymer. Thus, a polymer having a high molecular weight will require a lower percentage of polymer solids in the solution to provide a workable viscosity, and vice versa. Typically the polymer/solvent mixture must be heated strongly to achieve solution, as the polymer's crystallinity must be melted during the process of dissolution. In addition, mixed solvent systems may be used in order to eliminate most of the organic solvent use For example, a mixed solvent system may contain 95% water and 5% organic solvent, such as DMSO or N-methyl pyrrolidone. The presence of these slowly drying solvents may promote the development of enhanced polymer crystallinity relative to the all water systems. Under such slow-drying conditions, sufficient crystallinity may be promoted to render the coating stable, and the article may be used without a separate annealing step.

The selected article is then coated with the solvent/polymer system in any of the conventional methods in the art. For example, an article may be coated by spraying, dipping, painting or drawing through a die.

The article to be coated is any article that comes in contact with bodily fluids. Particularly, the bodily fluids that are contacted by these articles are blood, urine, gastrointestinal fluid and cerebrospinal fluids. Such articles include, for example, catheters, probes and implants such as pacemakers, artificial heat devices and mechanical sieves that are placed in a blood vessel to prevent travel of a clot to the brain or heart.

A particularly preferred article to be coated by the polymeric coating of this invention is a guidewire for use in assisting insertion of a catheter. Excellent coatings of guidewires may be made by drawing the wires through a polymer solution and then through a coating die where the combination of wire diameter, coating solution polymer concentration, and coating die inside diameter can be chosen so as to give the desired finished dry coating thickness. Drawing a wire through a cylindrical die will regulate the overall amount of coating material deposited on the wire, but does not assure that the coating thickness is uniform, as there is no easy way of keeping the wire centered in the die during the drawing process. Alternative die shapes, such as triangular or square, could keep wires centered and also allow some control of coating thickness. Preferably, the guidewire is coated to a thickness of between about 0.0001 inch (0.00254 mm) and about 0.0005 inch (0.0127 mm).

A second approach to coating guidewires is a variation of "dip coating". In this method, a wire to be coated is pulled through a solution of the polymer and withdrawn from the surface of the solution without a coating die to regulate the coating thickness. In this case, coating thickness is governed by the concentration of the solution and the amount of runoff Conditions may be adjusted so that runoff is largely occurring at a rate such that there is little or no runoff after the complete coating of the wire in order to avoid irregular coating thickness or waviness in the coatings.

After coating, the article is heat treated (annealed) to effect a crystallization of the polymer. This heat treatment of the coatings improves performance in both toughness and adherence, and surprisingly does so without an apparent loss in the surface slipperiness. The heat treatment reduces water swell of the coating but still produces a surface which, when wet, is highly slippery.

Heat treatment may be accomplished by heating in a convection oven, by microwave heating, or by heating with radiant energy. Typically, heating in a convection oven is done at a temperature of between about 100° and about 160° C. for between about 0.25 and about 4 hours. A preferred set of parameters for annealing in a convection oven is heating at a temperature of about 140° C. for about, 0.5 hour.

Air drying of the coating before heat treatment for a period of time of greater than about 3 hours is preferred. Air drying of the coating allows water to evaporate from the coating and curtails the development of bubbles during the annealing process.

When extra slipperiness is desired, a second coating of poly(vinyl alcohol) polymer may be applied to the article. This second coating need not be annealed, because it has been found that this second coating adheres well to the first annealed coating while at the same time providing increased slipperiness.

The following nonlimiting examples are further illustrative of the coatings and methods of this invention.

EXAMPLE 1

A 100% hydrolyzed poly(vinyl alcohol) polymer having a molecular weight of 115,000 (commercially available from Aldrich Chemical Company) was dissolved as 10% polymer solids by weight in water. Guidewires were obtained from Lake Region Manufacturing Co. (Chaska, MN) which were 5 feet (1.524 meters) in length, 0.037 inch (0.9398 mm) in diameter and made from bare stainless steel. These wires were drawn through the polymer solution in a U-shaped tube and then through a glass pipette having a tip inside diameter of 0.046 inches (1.168 mm), giving a wet coating thickness of approximately 0.0045 inches (0.1143 mm) and a dry coating thickness of approximately 0.00045 inches (0.01143 mm). The coatings were air dried and upon inspection found to be smooth surfaced When placed in water, the coated guidewires felt very slippery. Soaking in water overnight gave the water based coating a slightly blistered appearance and a slightly rough feel A sample of a guidewire coated as indicated above and not previously contacted with water was heated in an oven at 110° C. for about 1 hour and then placed in water to soak. Initial feel of the wire was smooth and slippery and soaking the wire in water overnight did not alter this appearance.

EXAMPLE 2

A guidewire was coated as in Example 1 except that the poly(vinyl alcohol) solution was prepared as 15% polymer solids by weight in DMSO. This coating gave a wet coating thickness of approximately 0.0045 inches (0.1143 mm) and a resulting dry coating thickness of approximately 0.00068 inches (0.0173 mm). Soaking an unheated wire in water overnight apparently did not adversely affect the DMSO based coating. When the coated wire was heated at 110° C. for about 1 hour, prior to soaking in water overnight, the wire still felt smooth, looked good and no blistering was visible.

EXAMPLE 3

A 100% hydrolyzed poly(vinyl alcohol) polymer having a molecular weight of 86,000 (commercially available from Aldrich Chemical Company) was dissolved in DMSO to give 10% solids by weight solution. This solution was filtered through a sintered glass filter with porosity size "D" to remove debris.

Guidewires of 0.034 inch (0.8636 mm) diameter stainless steel (commercially available from Lake Region Manufacturing Co.) were drawn through a polymer solution in a U-shaped tube. The wires were then drawn through a 17 gauge syringe needle (having inside diameter of 0.042 inch or 1.067 mm) giving a wet coating thickness of approximately 0.004 inches (0.1016 mm). The coated guidewires were air dried for 5 hours. The guidewires were then suspended in an oven and annealed for 2 hours at 105° C. These wires were found to be very slippery with no peel off.

EXAMPLE 4

A 100% hydrolyzed poly(vinyl alcohol) polymer having a molecular weight of 86,000 was dissolved in water to a 6% solids by weight solution. Stainless steel guidewires having a 0.035 inch (0.889 mm) diameter were dip coated by drawing the wire through the coating solution and exiting at a rate sufficiently slow to allow substantially complete runoff of the excess coating solution. The coated wires were air dried at ambient temperatures for 4 hours and then placed in a convection oven at 140° C. for 0.5 hour. The heat treated coated wires were removed from the oven and allowed to cool to room temperature.

The wires were divided into three groups. Wires in group A were saved as is for evaluation. Wires in group B were coated with a second coating of the poly(vinyl alcohol) solution using the same method and solution as the first layer, air dried for 3 hours and then heat treated at 110° C. for 0.5 hour. The wires of group C were coated with a second coating of the poly(vinyl alcohol) solution using the same method and solution as for the first coating layer and were then set aside for evaluation with no further heat treatment.

This overall experiment thus resulted in coated wires having outer surfaces with three differing levels of polymer crystallinity and therefore three differing levels of water uptake. The poly(vinyl alcohol) outer layer crystallinity should increase in the order of group C, which is less crystalline than group B, which in turn is less crystalline than group A. The water uptake of the outer layer of these coated wires should increase in the order of group A, which will take up water less than group B, which in turn will take up water less than group C. The three groups of wires were then evaluated for surface lubricity (slipperiness) by immersing the coated wires in water for a few minutes and observing the subjective slipperiness to the touch of the surfaces. It was very clear that the wires of group C were much slipperier than the wires of the other two groups, indicating that a surface coating of higher water swell appears to provide for a reduction in friction or an increase in surface lubricity. When this high level water swell surface coating is applied to an underlayer of heat treated poly(vinyl alcohol), the benefits of heat treating are observed for the overall bi-layer coating in the sense that the good adhesion of the hydrogel to the stainless steel associated with heat treatment is retained in the bi-layer coating. This is in contrast to simply coating guidewires with aqueous poly(vinyl alcohol) solution and omitting the heat treatment in order to obtain high water swell, because hydrogel coatings prepared in that manner do not adhere well to the metal surface.

EXAMPLE 5

PVA/Heparin Hydrogen—Preparation and Evaluation

A coating solution containing poly(vinyl alcohol) and heparin was prepared as follows: heparin (Sigma Chem. Co. H3125 heparin, 50 mg.) was dissolved in one ml. of distilled water. This solution was added to 3 ml. of a 10% by weight aqueous poly(vinyl alcohol) solution (prepared by dissolving poly(vinyl alcohol), Aldrich Chem. Co., 86,000 molecular weight, 100% hydrolyzed, 1 part, in 9 parts of distilled water followed by heating to 90° C.). The solution of heparin and poly(vinyl alcohol) in water was mixed thoroughly at room temperature to assure uniformity, and gave a perfectly clear solution. This solution was spread on a polished stainless steel panel in a thin film and allowed to dry; the coated panel was placed in an oven at 100° C. for 16 hours (overnight) and then removed and allowed to cool to room temperature. The coated panel was then placed in a solution of toluidene blue (1% aqueous solution of toluidine blue, obtained from Aldrich Chem. Co., which is a known stain for showing the presence of heparin, giving a magenta colored stain with heparin. The stained panel was then briefly rinsed with water to remove the excess toluidine blue stain, leaving the coating on the panel clearly stained a magenta color. This magenta colored coated panel was placed into water and allowed to soak. After one hour of soaking, there was no visible change in the coating and there was no color evident in the water. Addition of toluidine blue to the water used for soaking did not produce the magenta color characteristic of stained heparin but gave only the same blue color observed when adding the toluidine blue solution to distilled water (thus indicating that heparin is present in the poly(vinyl alcohol) layer and is not leaching into the water used for soaking). These tests were repeated after two hours and again after 24 hours with exactly the same results. As an additional control test, a poly(vinyl alcohol) coating on stainless steel in which there was no heparin present was treated with toluidine blue solution, followed by brief rinsing with water. All of the toluidine blue washed out of the coating, leaving a colorless coating, demonstrating that poly(vinyl alcohol) by itself does not cause the binding of the toluidine blue in the absence of the heparin. These experiments show that poly(vinyl alcohol) coatings which contain heparin, when heat-treated to anneal and crystallize the poly(vinyl alcohol) according to this invention, provide a hydrogel with heparin bound in the hydrogel coating, and that heparin does not leach or dissolve out of the coating, all in the absence of chemical cross-linking agents to link the heparin to the poly(vinyl alcohol).

EXAMPLE 6

(1) Tinting of Poly(Vinyl Alcohol) Hydrogel Coating

Stainless steel guidewires were coated with poly(vinyl alcohol) solution and heat treated as in Example 4, group A. The coated wires were then immersed for one hour in a solution of a tint prepared as follows. Remazol TM Brilliant Blue R (Sigma Chemical Co., St. Louis, MO, 0.313 g.) was dissolved in aqueous sodium phosphate solution (3.8 ml. of 10% aqueous solution of trisodium phosphate decahydrate) and this mixture war diluted with an additional 10 ml. of water. The wires were removed from the tinting solution and rinsed with running water. The tinted wires were a strong blue color. These tinted wires were placed in water at room temperature and allowed to soak overnight. The wires remained strongly blue tinted, and the soaking water remained colorless, indicating good non-leachability of the tinting. Similar tinting procedures were carried out with the following tints, reactive to hydroxyl-group containing polymers:

Remazol TM Brilliant Violet 5R
Reactive Green 5
Reactive Green 19
Reactive Red 4
Reactive Yellow 2
Reactive Blue 4

In all cases, the tints appear to react chemically with the coating and lead to strongly tinted coatings which show no tendency for the tint to leach out upon soaking. Thus a range of tints can be prepared as desired while using the heat-treated coatings of this invention. All of the above reactive tints were obtained from Sigma Chemical Co. from the 19S8 Biochemical and Organic Compounds Catalog.

(2) Preparation of a Tinted PVA to Use as a Coating Material

Poly(vinyl alcohol), 4.40 g. of 86,000 molecular weight, 100% hydrolyzed, was dissolved in water (39.6 g.) by heating to 90° C., followed by cooling to room temperature. Sodium phosphate solution (0.77 ml. of 10% aqueous trisodium phosphate decahydrate) and Remazol Brilliant Blue R (Sigma Chem. Co., 0.0834 g.) were added and the mixture was stirred to give uniform mixing. After 2 hours, the reaction mixture was poured into a large volume of methanol to precipate the tinted polymer. Filtration of the precipitated mixture allowed the isolation of a fibrous solid product, the tinted poly(vinyl alcohol), which was a strong blue material. This product was washed extensively with methanol to remove unreacted tint material, leaving a strongly blue material, which was then dissolved in water by heating to 90° C., giving a strongly blue coating solution. This tinted poly(vinyl alcohol) coating solution can then be used to coat wires or other devices by the processes of this invention.

I claim:

1. An article that comes into contact with bodily fluids wherein being slippery when wet is a desirable property of the article, which article is coated by a non-crosslinked, crystallized polymer or polymer blend comprising poly(vinyl alcohol) wherein said polymer or polymer blend is soluble before crystallization in water or DMSO at temperatures less than about 100°

C., and is stable in the presence of water at temperatures of up to about 60° C.

2. An article of claim 1 which is a guidewire.

3. An article of claim 1 which is an implant for the body.

4. An article of claim 1 wherein the implant is designed to be implanted in a blood vessel.

5. The article of claim 1 wherein the polymer has a degree of crystallinity of between about 30 and about 50 percent.

6. The article of claim 5 wherein the polymer has a degree of crystallinity of between about 40 and about 45 percent.

7. An article of claim 1 wherein the poly(vinyl alcohol) polymer is more than 88% hydrolyzed before crystallization.

8. An article of claim 1 wherein the poly(vinyl alcohol) polymer has a molecular weight of between about 14,000 and about 1,000,000.

9. An article of claim 1 wherein the poly(vinyl alcohol) polymer has a molecular weight of about 40,000 to about 126,000.

10. An article of claim 1 wherein the poly(vinyl alcohol) polymer has a molecular weight of about 80,000 to about 115,000.

11. An article of claim 1 which additionally comprises heparin.

12. An article of claim 1 which additionally comprises a dye or tint.

13. An article of claim 12 wherein the dye is covalently bonded to the poly(vinyl alcohol) polymer.

* * * * *